United States Patent [19]

Allen

[11] 4,188,189

[45] Feb. 12, 1980

[54] QUANTITATIVE TESTING FOR VITAMIN $B_{12}$

[75] Inventor: Robert H. Allen, Englewood, Colo.

[73] Assignee: University Patents, Inc., Norwalk, Conn.

[21] Appl. No.: 893,524

[22] Filed: Apr. 4, 1978

[51] Int. Cl.$^2$ .................. G01N 33/16; G01N 31/06
[52] U.S. Cl. .................. 23/230.3; 23/230 B; 23/230.6; 424/1; 424/96; 435/7
[58] Field of Search ............ 23/230 B, 230.3, 230.6; 424/1, 1.5, 96; 195/2

[56] References Cited

U.S. PATENT DOCUMENTS

| | | | |
|---|---|---|---|
| 3,434,927 | 3/1969 | Highley | 195/2 |
| 3,442,819 | 5/1969 | Herbert | 210/31 R |
| 3,937,799 | 2/1976 | Lewin | 424/1 |

Primary Examiner—Sidney Marantz
Attorney, Agent, or Firm—Donald W. Margolis

[57] ABSTRACT

Errors in the radioisotope dilution assay (RIDA) of the vitamin $B_{12}$ level of human blood have been traced to the presence of vitamin $B_{12}$ analogues. These previously unrecognized analogues bind with proteins normally included with binding proteins used in the prior art RIDA techniques. The errors caused by the $B_{12}$ analogues are avoided by using a composition for binding vitamin $B_{12}$ which is substantially free of substances which bind vitamin $B_{12}$ analogues. Moreover, by using both types of binders in separate assays, the amount of analogue present may be arrived at by taking the difference of the assays. Compositions that are effectively substantially pure intrinsic factor (IF) are used as binders.

6 Claims, No Drawings

QUANTITATIVE TESTING FOR VITAMIN $B_{12}$

The invention described herein was made, in part, in the course of work under a grant or award from the Department of Health, Education, and Welfare.

BACKGROUND OF THE INVENTION

1. Field of the Invention

The present invention relates to methods and materials for assaying mammalian blood and tissue. More specifically it relates to methods and materials for determining the amounts of vitamin $B_{12}$ and vitamin $B_{12}$ analogues in human plasma.

2. Prior Art

For many years it has been recognized that the assay of the vitamin $B_{12}$ level in humans is a valuable technique for diagnosing and subsequently treating certain diseases, such as for example, pernicious anaemia, post gastrectomy states nutritional deficiencies, intestinal disorders, and others. Initially, vitamin $B_{12}$ was assayed microbiologically using either *Euglena gracilis* or *Lactobacillus leichmannii*. More recently, radioisotope dilution (RID) assays for $B_{12}$ have been utilized. Such radioisotope dilution assay techniques are well documented in the literature, see for example Lau, et.al. (1965) "Measurement of Serum $B_{12}$ Levels Using Radioisotope Dilution and Coated Charcoal," BLOOD, 26, 202, as modified by Raven et.al. (1968) "The Effect of Cyanide Serum and Other Factors on the Assay of Vitamin $B_{12}$ by Radio-Isotope Method Using $^{57}Co$-$B_{12}$, Intrinsic Factor and Coated Charcoal," GUYS HOSPITAL REPORTS, 117, 89; and (1969) "Improved Method for Measuring Vitamin $B_{12}$ in Serum Using Intrinsic Factor, $^{57}Co$-$B_{12}$ and Coated Charcoal," JOURNAL OF CLINICAL PATHOLOGY, 22, 205.

Such prior art radioisotope dilution assay of vitamin $B_{12}$ generally includes the steps of freeing the endogenous $B_{12}$ from its natural binding protein by boiling at a selected pH and then adding a measured amount of the radioisotope $^{57}Co$-$B_{12}$ and a limited amount of binding protein. All of the binding protein will be bound by some form of $B_{12}$ since the amount of radioisotope $B_{12}$ added is, by itself, sufficient to bind the small amount of protein. As both the natural $B_{12}$ and the radioactive $B_{12}$ compete to bind with the protein, the degree to which the radioactive count of the protein bound $B_{12}$ was inhibited was thought to be indicative of the amount of natural $B_{12}$ present in the sample undergoing testing.

More specifically, in the technique of Lau et.al. as modified by Raven et.al., serum $B_{12}$ is separated from binding protein in the plasma sample by boiling with 0.25 N HCl. Radioisotope $B_{12}$ is added to the reaction mixture and the $B_{12}$ mixture is reacted with protein, normally in the form of a commercially available binder. Then the free or unbound $B_{12}$ is separated from the protein bound $B_{12}$ by protein-coated charcoal and the radioactivity of the supernatant liquid containing the mixture of bound radioactive $B_{12}$ and bound non-radioactive $B_{12}$ counted for radioactivity. The serum $B_{12}$ concentration is then calculated from the count, often by comparison with a standard chart. Almost as soon as this technique began to be utilized it was recognized that the vitamin $B_{12}$ measurements it provided were usually inconsistent with the results obtained by other measuring techniques for $B_{12}$, such as the microbiological assays. Most often, the vitamin $B_{12}$ assay obtained by radioisotope dilute techniques have been found to be high. Many theories have been advanced to explain the cause of the high vitamin $B_{12}$ readings. However, it is believed that nowhere in the prior art is it recognized that there are substances in mammalian blood and tissue which react with certain non-specific protein binders in the radioisotope dilution assay techniques to provide an analysis of vitamin $B_{12}$ which is apparently higher than the amount of $B_{12}$ actually in the sample. Additionally, it is believed that nowhere in the prior art is it recognized that most common and commercial RID assay protein binders are not specific to vitamin $B_{12}$, but that they are also capable of binding with the heretofore unknown $B_{12}$ analogues and thus provide erroneous $B_{12}$ assays.

BRIEF DESCRIPTION OF THE INVENTION

As has already been indicated, in the standard radioisotope binding assay for vitamin $B_{12}$, a known amount of radioactive vitamin $B_{12}$ is mixed with a prepared to-be-tested sample. Then, a known, but extremely limited, amount of protein which is capable of binding with both the natural and radioactive vitamin $B_{12}$ is added to the mixture. Then, utilizing well known techniques, the radioactivity of the bound sample is compared, for example, with a standard curve to determine the amount of natural vitamin $B_{12}$ present in the tested sample. Such standard curves are initially established for use in RID assay, for example, by measuring the amount of bound radioactive $B_{12}$ in the presence of the same type and amount of protein binder, but with several different amounts of known non-radioactive $B_{12}$.

It has now been discovered, for what is believed to be the first time, that mammalian blood and tissue contain materials other than vitamin $B_{12}$ which couple with certain binding proteins which are commonly used in RID assays. For purposes of this specification and claims the non-vitamin $B_{12}$ materials which are capable of binding with such proteins will be herein referred to as "vitamin $B_{12}$ analogues," "$B_{12}$ analogues" or simply as "analogues." They are referred to as analogues, not due to their chemical structure, which is not known with certainty, nor in the commonly accepted chemical sense of the word "analogue." Rather they are referred to as analogues due to their reactivity with the binding proteins commonly used in RID assays. As will be shown in more detail, hereinafter, there are other similarities which have been discovered between vitamin $B_{12}$ and the newly discovered analogues which are present in mammalian blood and tissue.

After the presence of $B_{12}$ analogues was discovered it was then determined that protein binders commonly present in RID assays were: (1) Non-specific in binding to only vitamin $B_{12}$; and (2) reactive in binding with both vitamin $B_{12}$ and $B_{12}$ analogues; and (3) capable of reacting with both $B_{12}$ and $B_{12}$ analogues independent of pH. These are most commonly R proteins. Additionally, it has been determined that other protein binders, are: (1) Very specific in their reactivity substantially only with vitamin $B_{12}$; (2) substantially non-reactive with the $B_{12}$ analogues; and (3) non-reactive with either vitamin $B_{12}$ or $B_{12}$ analogues in highly acid environments. These are most commonly proteins in the form of pure human intrinsic factor (IF), hog IF, rabbit IF, other IFs and vitamin $B_{12}$ specific binders.

In the past the problem has been that RID binders include substantial amounts of protein which is not specific to vitamin $B_{12}$. Therefore, the radioisotope dilution assay utilizing that binder on samples which contain $B_{12}$ analogues will produce a measurement which indicates a greater amount of $B_{12}$ present in the plasma than exists in fact. As will be shown in more detail hereinafter, commercially available protein binders, which have heretofore been labeled as containing intrinsic factor, in fact include only about 10% to about 30% intrinsic factor protein, while the balance of the protein in the binder is of a non-specific type, such as R protein. Thus, the protein materials in the commercial protein binders are capable of indiscriminate reaction with the heretofore unrecognized vitamin $B_{12}$ analogue materials in mammalian blood and tissue. These extraneous reactions give RID analyses having the appearance of apparently higher vitamin $B_{12}$ content than the samples in fact contain. This is due to the fact that when the binder includes protein which is non-specific to vitamin $B_{12}$ and which is capable of reacting with both vitamin $B_{12}$ and $B_{12}$ analogues, then the use of this protein in the radiobinding assay measures both the vitamin $B_{12}$ and the vitamin $B_{12}$ analogues which are present in the sample. However, in accordance with the present invention, when the proteins which are utilized are substantially specific to vitamin $B_{12}$, such as substantially pure intrinsic factor, then in the RID assay one binds and measures substantially only the vitamin $B_{12}$ in the sample, without the measurement of extraneous $B_{12}$ analogues. This provides a more accurate vitamin $B_{12}$ RID assay.

Based on these discoveries it is proposed that in the practice of RID assay only protein which is specific in its reaction to vitamin $B_{12}$ be utilized. Alternatively, it is proposed that mixtures of vitamin $B_{12}$ specific and non-specific binding proteins be treated, for example, with an excess of material such as $B_{12}$ analogues, which will bind or inactivate only the non-specific binding proteins, prior to the material's use in RID assays, so that the non-specific protein will be substantially unavailable for reaction with any vitamin $B_{12}$ or analogues in a sample when the RID assay is conducted. In yet another modification of the present invention, crude binder, including non-specific binding proteins, is subjected to proteolytic enzyme treatment prior to utilization as a vitamin $B_{12}$ binder in RID assays. Such proteolytic enzyme treatment destroys the binding ability of the non-specific proteins without destroying the binding ability of the proteins which are specific to vitamin $B_{12}$.

Utilizing the techniques of the present invention, the $B_{12}$ analogues can be assayed by analyzing the amount of vitamin $B_{12}$ present uitlizing, for example, a vitamin $B_{12}$ specific binder, then assaying the sample utilizing a non-specific binder and determining the difference between the two assays as a measure of the amount of vitamin $B_{12}$ analogues present.

These and other techniques are readily determined, once, as taught for the first time by the present invention, the presence of $B_{12}$ analogues in mammalian blood and tissue is recognized.

The foregoing and other objects, features and advantages of the invention will be apparent from the following more particular description of preferred embodiments of the invention.

DETAILED DESCRIPTION OF THE INVENTION

In the following examples and tables certain chemical components were utilized. For ease of communication they have been given shortened names in the text. The concordance between the "component" names and their actual compositions is as follows:

| Components | Actual Composition |
|---|---|
| A. Buffer | 1.0M Tris (hydroxymethyl) aminomethane-HCl pH 10.0 |
| B. Albumin | Bovine serum albumin, 2 mg per ml in $H_2O$ |
| C. Salt | 0.15M NaCl |
| D. Boiled buffer | (1 part) 0.5M sodium acetate-HCl pH 4.5 (1 part) 0.01M $KPO_4$ pH 7.5, 0.15M NaCl (2 parts) 50 µg per ml KCN in 0.15M NaCl The complete solution is heated for 45 min. at 100° C. |
| E. Standard (100 pg/ml $B_{12}$) | Solution D containing 100 pg per ml vitamin $B_{12}$. The solution is heated for 45 min. at 100° C. after the vitamin $B_{12}$ is added. The concentration of vitamin $B_{12}$ in the stock solution used to make component E is determined by its light absorbance at 278, 361 and 550 nm. |
| F. Standard (1000 pg/ml $B_{12}$) | Same as component E except that the vitamin $B_{12}$ concentration is 1000 pg/ml. |
| G. ($^{57}Co$) $B_{12}$ | 1000 pg per ml of ($^{57}Co$) $B_{12}$, (150–300 uCi/ug), in $H_2O$. |
| H. Binder | Present in 0.01M Tris-HCl pH 8.2, containing 0.15M NaCl and 50 ug per ml bovine serum albumin. Binders are diluted in this solution to reach a concentration of 700 pg per ml of vitamin $B_{12}$ binding ability. Individual binders are as follows: (1) Human intrinsic factor (Human IF) - Human gastric juice containing more than 95% intrinsic factor based on assays employing inhibition of vitamin $B_{12}$ binding with anti-intrinsic factor antibodies (>95% inhibition) and cobinamide (<5% inhibition). (2) Human R protein (Human R) - Human saliva containing more than 95% R protein based on assays employing inhibition of vitamin $B_{12}$ binding with cobinamide (>95% inhibition) and anti-intrinsic factor antibodies (<5% inhibition) (3) Hog intrinsic factor (Hog IF) - This protein was purified from "Hog intrinsic factor concentrate" by affinity chromatography on vitamin $B_{12}$-Sepharose employing gradient elution with guanidine-HCl followed by gel filtration. The final preparation contained more than 95% intrinsic factor based on assays employing inhibition of vitamin $B_{12}$ binding with anti-intrinsic factor antibodies (>95% inhibition) and cobinamide (<5% inhibition). (4) Hog R protein (Hog R) (Also designated in the scientific literature as Hog non-intrinsic factor) - This protein was purified from "Hog intrinsic factor concentrate" as described above in 3). The final preparation contained more than 95% R protein based on assays employing inhibition of vitamin $B_{12}$ binding with anti-intrinsic factor antibodies (<5% inhibition) and cobinamide (>95% inhibition). (5) Rabbit intrinsic factor (Rabbit IF) - An extract of rabbit gastric mucosa containing more than 95% intrinsic factor based on assays employing inhibition of vitamin $B_{12}$ binding with anti-intrinsic factor antibodies (>95% inhibition) and cobinamide (<5% inhibition). (6) Hog intrinsic factor concentrate (Hog IFC) - A crude extract of hog pyloric mucosa. It contained 25% Hog IF and 75% Hog R based on assays employing inhibition of vitamin $B_{12}$ binding with anti-intrinsic factor antibodies (25% inhibition) and cobinamide (75% inhibition). (7) Hog IFC + Cobinamide - Hog IFC contain- |

| Components | Actual Composition |
|---|---|
| | ing the vitamin $B_{12}$ analogue cobinamide ([CN, OH]Cbi) in a molar amount equal to 100 times the total vitamin $B_{12}$ binding ability, i.e. a 100 fold excess of cobinamide. |
| | (8) Hog IFC + CN-Cbl [bde-OH] - The same as item (7) above except that the analogue added is CN-Cbl [bde-OH] and is present in a 1000 fold molar excess. |
| | (9) Hog IFC + [3,5,6-Me$_3$BZA] (CN, OH)Cba- The same as item (7) above except that the analogue added is [3,5,6-Me$_3$BZA] (CN, OH)Cba. |
| | (10) Digested Hog IFC - Hog IFC incubated with bovine pancreatic trypsin (2 mg per ml) and bovine pancreatic chymotrypsin (2 mg per ml) for 60 min. at 37° C. |
| I. Charcoal | A solution containing 25 mg per ml neutral charcoal (Norit) and 5 mg per ml bovine serum albumin in $H_2O$. |
| J. unknown sample | Samples containing unbound vitamin $B_{12}$ are diluted in solution D (see above). Samples containing bound vitamin $B_{12}$, such as serum, are prepared as follows: (1 part) sample (1 part) 0.5M sodium acetate-HCl pH 4.5 (2 parts) 50 ug per ml KCN in 0.15M NaCl The complete mixture is heated at 100° C. for 45 min. followed by centrifugation at 5000 × g at 4° C. for 20 min. The supernatant is removed and used for assay. |

Each of the RID assays referred to herein utilized the components referred to above. The method and order of utilizing the components is that set forth in Table I. That is, components A, B, C, etc. or the buffer, albumin, and salt, respectively, etc. were added in the order, from left to right, shown in Table I.

Table I

Flow Sheet for Radiobinding Assay for Vitamin $B_{12}$

| Tube # | A Buffer (μl) | B Albumin (μl) | C Salt (μl) | D Boiled Buffer (μl) | E Standard 100pg/ml $B_{12}$ (μl) | F Standard 1000pg/ml $B_{12}$ (μl) | J Unknown Sample (μl) | G [$^{57}$Co] $B_{12}$ (μl) | H Binder (μl) | I Charcoal (μl) |
|---|---|---|---|---|---|---|---|---|---|---|
| 1,2 | 225 | 50 | 875 | 800 | — | — | — | 50 | — | — |
| 3,4 | 225 | 50 | 375 | 800 | — | — | — | 50 | — | 500 |
| 5,6 | 225 | 50 | 325 | 800 | — | — | — | 50 | 50 | 500 |
| 7 | 225 | 50 | 325 | 720 | 80 | — | — | 50 | 50 | 500 |
| 8 | 225 | 50 | 325 | 640 | 160 | — | — | 50 | 50 | 500 |
| 9 | 225 | 50 | 325 | 560 | 240 | — | — | 50 | 50 | 500 |
| 10 | 225 | 50 | 325 | 300 | 500 | — | — | 50 | 50 | 500 |
| 11 | 225 | 50 | 325 | 720 | — | 80 | — | 50 | 50 | 500 |
| 12 | 225 | 50 | 325 | 640 | — | 160 | — | 50 | 50 | 500 |
| 13 | 225 | 50 | 325 | 450 | — | 350 | — | 50 | 50 | 500 |
| 14 | 225 | 50 | 325 | — | — | 800 | — | 50 | 50 | 500 |
| Unknown Sample | 225 | 50 | 325 | — | — | — | 800 | 50 | 50 | 500 |

After the addition of $^{57}$Co-$B_{12}$ the components are mixed thoroughly to mix both the naturally occurring $B_{12}$ and the radioisotope $B_{12}$ to make them compete and equally available to react with the binder. After the addition of the binder, H, the components were again mixed thoroughly, and then incubated for 45 minutes at about 37° C. Charcoal was then added to the incubated mixture and the components again mixed thoroughly and incubated for another 5 minutes at room temperature. This was followed by centrifuging at 2000×g at 4° C. for 30 minutes. Then 1000 ul of the resulting supernatant liquid is pipetetted from the sample and a determination of the amount of $^{57}$Co-$B_{12}$ present is made. The amount of $^{57}$Co-$B_{12}$ is indicative of the amount of natural $B_{12}$ in the tested sample, with lesser amounts of $^{57}$Co-$B_{12}$ being indicative of greater amounts of natural vitamin $B_{12}$ in the sample.

Calculations of vitamin $B_{12}$, utilizing the data obtained in the foregoing manner, is made as follows:

Calculation of data from radiobinding assay for plasma vitamin $B_{12}$ assay as outlined in Table I (1) The values in tubes 3 and 4, the "blank" tubes without binder are averaged and subtracted from all other tubes starting with tube 5.

(2) The background radiation is subtracted from tubes 1 and 2 and these values are averaged.

(3) Tubes 5 and 6 are averaged. This value should be at least 15% below the average values for tubes 1 and 2 to insure that all of the binder is saturated in the presence of ($^{57}$Co) $B_{12}$ alone.

(4) Values for each tube beginning with tube 7 are divided by the average of tubes 5 and 6 to give values for "% trace binding."

(5) Percent trace binding for tubes 7–14 are used to obtain a standard curve. We plot % trace binding on the ordinate of logit-log paper versus pg vitamin $B_{12}$ on the log scale.

(6) The amount of vitamin $B_{12}$ in unknown samples is determined by interpolation from the standard curve or data of % trace binding versus pg vitamin $B_{12}$.

(7) The standard curves for all of the various binders used are virtually indistinguishable and vary little from day to day. Nevertheless, a complete standard curve is always obtained for every binder with each set of assays. Representative data obtained with the assays are present in Table II.

Table II

Standard Curves obtained with the radiobinding assay for vitamin $B_{12}$ using various binders

| | % trace binding observed with various binders[b] | | | | |
|---|---|---|---|---|---|
| Vitamin $B_{12}$ added[a] (pg) | Human IF | Human R | Hog IF | Hog R | Hog IFC |
| 0 | (100) | (100) | (100) | (100) | (100) |
| 8 | 90 | 93 | 94 | 89 | 89 |
| 16 | 85 | 84 | 83 | 83 | 80 |
| 24 | 79 | 78 | 74 | 76 | 76 |
| 50 | 64 | 60 | 58 | 56 | 59 |
| 80 | 45 | 44 | 44 | 43 | 43 |
| 160 | 30 | 28 | 28 | 27 | 28 |
| 350 | 15 | 14 | 15 | 14 | 14 |

Table II-continued

Standard Curves obtained with the radiobinding assay for vitamin $B_{12}$ using various binders

| Vitamin $B_{12}$ added[a] (pg) | % trace binding observed with various binders[b] | | | | |
|---|---|---|---|---|---|
| | Human IF | Human R | Hog IF | Hog R | Hog IFC |
| 800 | 6 | 6 | 7 | 6 | 7 |

[a] The vitamin $B_{12}$ was boiled for 45 min. at 100° C. in the same solution used to extract endogenous vitamin $B_{12}$ from human plasma.
[b] Assays were performed on different days.

Evidence as to the Origin and Existence of Vitamin $B_{12}$ Analogues in Mammalian Blood and Tissue Once the problem of the prior art is recognized, that is, that there are vitamin $B_{12}$ analogues present in mammalian blood and tissue, it becomes a relatively simple matter to prove the existence and chemistry of such analogues. It is also appropriate to prove that the various steps of the RID assay do not cause the $B_{12}$ analogues to be formed, for example, from vitamin $B_{12}$.

In one instance this has been most convincingly shown by obtaining pure crystalline vitamin $B_{12}$, subjecting various known concentrations of it to the same conditions used to extract endogenous vitamin $B_{12}$ from blood and tissue samples (boiling for 45 minutes in the same extraction solution) and then analyzing them by RID assay using several binding proteins, for example, in the form of human IF, hog IF, human R, hog R and hog IFC on different portions of the same extracted vitamin $B_{12}$ samples.

Referring to Table II, it will be seen that when various known amounts of pure vitamin $B_{12}$, ranging from about 8 pg to about 800 pg were tested with various protein binders, that in each instance, the percent of radioactive trace binding, or more accurately, the inhibition of $^{57}Co-B_{12}$ binding, observed was substantially the same for each binder. It is thus seen, that regardless of which protein binder is utilized, the percent binding, i.e. inhibition of the ($^{57}Co$)-$B_{12}$ is substantially the same. This is indicative of the fact that during preparation for RID assay the pure vitamin $B_{12}$ was not converted to analogues of the type which have now been observed in mammalian blood and tissue. It is also indicative of the fact that in the absence of interferring masking components in the samples, such as $B_{12}$ analogues, any of the binding proteins can be utilized to provide substantially equally accurate RID assays of vitamin $B_{12}$. Furthermore, the data in Table II should be suitable as a standard in the determination of vitamin $B_{12}$ by the same RID assay.

By comparison, when endogenous vitamin $B_{12}$ was extracted from serum from 74 normal blood donors (37 women, 37 men, ages 17–61) and tested utilizing the same binding proteins with the exception of hog IFC which was not used, the results were quite different. In every case in which serum from normal donors was tested greater inhibition of $^{57}Co-B_{12}$, and therefore greater apparent vitamin $B_{12}$, was observed with assays employing, as the binder, human R or hog R than was observed with assays employing human IF or hog IF. The data on the 74 normal donors is included in Table III.

Table III

Distribution of a serum vitamin $B_{12}$ values as measured with various binders for 74 normal subjects and 21 patients with clinical evidence of vitamin $B_{12}$ deficiency
All assays were performed at pH 9.0

| Serum Vitamin $B_{12}$ (pg/ml) | Human R | | Hog R | | Human IF | | Hog IF | | Human R minus Human IF | | Hog R minus Hog IF | |
|---|---|---|---|---|---|---|---|---|---|---|---|---|
| | Normals | Patients | Normals | Patients | Normals | Patients | Normals | Patients | Normals | Patients | Normals | Patients |
| 0–24 | | | | | | 8 | | 11 | | | | |
| 25–49 | | | | | | 6 | | 5 | | | | |
| 50–74 | | | | | | 5 | | 3 | | 1 | 2 | 1 |
| 75–99 | | 1 | | 1 | | 2 | | 2 | 2 | | 3 | |
| 100–124 | | 2 | | 1 | | | | | 2 | 3 | 9 | 3 |
| 125–149 | | 2 | | 5 | 4 | | 1 | | 7 | 3 | 5 | 3 |
| 150–174 | | 3 | | 1 | 5 | | 3 | | 6 | 5 | 9 | 5 |
| 175–199 | | 4 | | 3 | 2 | | 3 | | 6 | 3 | 8 | 3 |
| 200–224 | 1 | 1 | | 2 | 5 | | 4 | | 8 | 2 | 11 | 2 |
| 225–249 | | 3 | 1 | 1 | 6 | | 4 | | 2 | 3 | 6 | 3 |
| 250–274 | | | | 3 | 10 | | 9 | | 10 | | 4 | |
| 275–299 | | 1 | 2 | 1 | 4 | | 3 | | 5 | | 1 | |
| 300–324 | 1 | 2 | 4 | 2 | 12 | | 4 | | 6 | | 3 | |
| 325–349 | 3 | 1 | 2 | 1 | 5 | | 6 | | 4 | 1 | 5 | 1 |
| 350–374 | 5 | 1 | 1 | | | | 10 | | 4 | | 1 | |
| 375–399 | 3 | | 2 | | 3 | | 4 | | 4 | | 2 | |
| 400–424 | 5 | | 3 | | 4 | | 5 | | 5 | | 1 | |
| 425–449 | 3 | | 4 | | 3 | | 2 | | 2 | | | |
| 450–474 | 4 | | 6 | | 2 | | 3 | | | | 1 | |
| 475–499 | 5 | | 5 | | | | 3 | | | | 1 | |
| 500–524 | 7 | | 4 | | 1 | | 3 | | | | | |
| 525–549 | 3 | | 4 | | 1 | | | | | | | |
| 550–574 | 5 | | 3 | | 2 | | 1 | | | | 1 | |
| 575–599 | 1 | | 2 | | 1 | | | | 1 | | | |
| 600–624 | 2 | | 4 | | 1 | | 3 | | | | 1 | |
| 625–649 | 5 | | 4 | | | | | | | | | |
| 650–674 | 3 | | 3 | | 2 | | | | | | | |
| 675–699 | 2 | | 3 | | | | | | | | | |
| 700–724 | 3 | | 6 | | | | 1 | | | | | |
| 725–749 | 2 | | | | | | | | | | | |
| 750–774 | 3 | | 1 | | | | 1 | | | | | |
| 775–799 | | | 1 | | 1 | | | | | | | |

Table III-continued

Distribution of a serum vitamin $B_{12}$ values as measured with various binders for 74 normal subjects and 21 patients with clinical evidence of vitamin $B_{12}$ deficiency
All assays were performed at pH 9.0

| Serum Vitamin $B_{12}$ (pg/ml) | Human R | | Hog R | | Human IF | | Hog IF | | Human R minus Human IF | | Hog R minus Hog IF | |
|---|---|---|---|---|---|---|---|---|---|---|---|---|
| | Nor-mals | Pa-tients | Nor-mals | Pa-tients | Nor-mals | Pa-tients | Nor-mals | Pa-tients | Nor-mals | Pa-tients | Nor-mals | Pa-tients |
| 800–824 | | | 2 | | | | | | | | | |
| 825–849 | | | | | | | | | | | | |
| 850–874 | 1 | | 1 | | | | | | | | | |
| 875–899 | 1 | | 2 | | | | 1 | | | | | |
| 900–924 | 1 | | 1 | | | | | | | | | |
| 925–949 | 2 | | 1 | | | | | | | | | |
| 950–974 | 1 | | | | | | | | | | | |
| 975–999 | 1 | | | | | | | | | | | |
| 1000–1024 | | | | | | | | | | | | |
| 1025–1049 | | | | | | | | | | | | |
| 1050–1074 | 1 | | | | | | | | | | | |
| 1075–1099 | | | | | | | | | | | | |
| 1100–1124 | | | | | | | | | | | | |
| 1125–1149 | | | 1 | | | | | | | | | |
| 1150–1174 | | | | | | | | | | | | |
| 1175–1199 | | | | | | | | | | | | |
| 1200–1224 | | | | | | | | | | | | |
| 1225–1249 | 1 | | | | | | | | | | | |
| range of serum $B_{12}$ | 220–1230 | 85–355 | 245–1135 | 84–342 | 130–785 | 0–78 | 135–880 | 0–86 | 70–575 | 56–337 | 50–605 | 72–332 |
| mean of serum $B_{12}^{(a)}$ | 576 | 205 | 573 | 204 | 322 | 36 | 361 | 33 | 254 | 169 | 212 | 171 |
| mean ± 2 Std. Dev. | 282–1040 | - | 276–1065 | 136– | 157–656 | | 70–717 | | 58–661 | | 531 | |

$(a)$ Based on values obtained with log vitamin $B_{12}$. Log values were used since these gave a normal curve while the curve using untransformed values were skewed to the right.

Other data concerning patients with diagnosed vitamin $B_{12}$ deficiencies are present, and comparisons between the normal donors and patients have also been made on Table III, and will be discussed in more detail hereinafter. Referring to Table III it is seen that the mean endogenous vitamin $B_{12}$ RID assay levels, in terms of pg of vitamin $B_{12}$ per ml of serum, are 548 and 542 for human R and hog R, respectively, but only 298 and 336 for human IF and hog IF, respectively. This demonstrates that something is present in extracts of normal human serum which inhibits the vitamin $^{57}Co$-$B_{12}$ binding ability of human R and hog R to a greater extent than it inhibits the binding ability of human IF and hog IF. Under current RID assay techniques the greater inhibition which is found using human R and hog R is analyzed to indicate a higher vitamin $B_{12}$ content. It is those substances, which have now been found to be present in human blood serum and which preferentially inhibit $^{57}Co$-$B_{12}$ binding of human R and hog R, which have been herein denominated as "vitamin $B_{12}$ analogues."

Chemical Nature and Properties of Vitamin $B_{12}$ Analogues

The vitamin $B_{12}$ analogues, which are herein for the first time identified as being present in mammalian blood and tissue, have been isolated by paper chromatography and compared with pure vitamin $B_{12}$. Vitamin $B_{12}$ and the so-called "vitamin $B_{12}$ analogues" were found to have the following properties in common: (1) Both were adsorbed to charcoal and remained adsorbed when the charcoal was washed with 5% phenol; (2) Both were eluted from charcoal when the charcoal was washed with 67% acetone; (3) Both were extracted from aqueous solution into phenol and remained in the phenol phase even when the phenol was washed repeatedly with water; (4) Both passed into the aqueous phase when the phenol layer was dissolved in an excess of diethyl ether; (5) Both eluted with similar apparent molecular weights (approximately 1356) during gel filtration on columns of Bio-Rad P-4 polyacrylamide; (6) Both were adsorbed to a column of Sepharose-2B agarose that contained covalently bound hog R protein and both remained bound when the column was washed with 0.1 M glycine-NaOH pH, 10.0, 1.0 M NaCl, and both were eluted from the Sepharose with either 85% phenol or 60% pyridine. Because of these similarities the newly discovered material is seen to be similar to vitamin $B_{12}$ and is thus referred to as vitamin $B_{12}$ analogue.

The chemical nature and structure of the newly discovered vitamin $B_{12}$ analogues which are now found to be present in mammalian blood and tissue is not known. An effort was made to compare them with chemically ture forms of vitamin $B_{12}$, sometimes referred to in the literature as analogues of vitamin $B_{12}$, namely $CN$-$B_{12}$, $OH$-$B_{12}$, adenosyl-$B_{12}$ and $CH_3$-$B_{12}$, already known to be present in serum and tissues. This was done by adding 500 pg of each of these four known forms of vitamin $B_{12}$ to four different portions of the same human serum, in the dark. Prior to the additions the serum contained 250 pg and 450 pg of vitamin $B_{12}$ as assayed by RID using human IF and human R, respectively, thus exhibiting a difference of 200 pg. After addition of the materials to the serum, each was allowed to incubate in the dark for 15 minutes to allow binding of the added known forms of vitamin $B_{12}$ to the binding proteins normally present in the serum. Then the serum, with the added forms of vitamin $B_{12}$ was extracted utilizing standard conditions and the apparent amount of vitamin $B_{12}$ assayed by RID utilizing both human R protein and human IF protein. Both the human R and human IF assays showed an increase in the apparent amount of vitamin $B_{12}$ of about 500 pg. However, the original difference observed between the values obtained with the human R protein and the human IF protein, i.e. 200 pg, did not change. If any of the added known forms of vitamin $B_{12}$ in the human serum had been converted to the newly discovered analogues, then the assays would have shown an increase in the difference. This provides evidence that the newly discovered vitamin $B_{12}$ analogues were not formed from any of the known endogenous forms of native vitamin $B_{12}$ during the extraction procedure.

Isolation of Vitamin $B_{12}$ Analogue

The materials which are herein designated as "vitamin $B_{12}$ analogues" and which have been found to preferentially inhibit R proteins in the vitamin $B_{12}$ assays were substantially separated from endogenous vitamin $B_{12}$ by the following purification shceme. A trace amount of 150 pg $^{57}Co-B_{12}$, was added to 1800 ml of freshly collected normal human plasma. The added $^{57}Co-B_{12}$ was sufficiently small that it did not interfere with subsequent RID assays. After incubating at room temperature for 30 minutes the vitamin $B_{12}$ was extracted and assayed under standard conditions. When human IF binder was utilized in the RID assay the extract was found to contain 1050 ng of vitamin $B_{12}$, but when human R protein was utilized as the binder it appeared to contain 2030 ng of vitamin $B_{12}$, almost twice as much vitamin $B_{12}$. The extract was then passed through a column of Sepharose containing covalently bound hog R protein. The column retained greater than 99% of the $^{57}Co-B_{12}$ as well as the endogenous vitamin $B_{12}$ as assayed by RID with human IF or human R protein. After the column was washed with a variety of buffers and water the material was eluted with 60% pyridine, taken to dryness under vacuum, dissolved in water, and adsorbed onto charcoal. The charcoal was washed with 5% phenol followed by water and the mixture of vitamin $B_{12}$, $^{57}Co-B_{12}$ and analogue $B_{12}$ was eluted from the charcoal with 67% acetone. The material was again taken to dryness under vacuum, dissolved in water, and then separated utilizing 19 inch long Whatman 3 MM paper for paper chromatography and a solvent system consisting of 800 ml sec-butanol, 8 ml glacial acetic acid, 6 mmol HCN and 400 ml water. The chromatography was performed in the descending manner for 30 hours at room temperature in an environment that inhibited evaporation of the solvent. The paper chromatogram was allowed to dry in a fume oven and divided into 38 one-half inch fractions and numbered, with fraction 1 starting at the point of applicaion and number 38 being at the lowest point on the chromatogram. Each one-half inch fraction was then incubated with 5 ml of water at 4° C. for twelve hours to elute the vitamin $B_{12}$, $^{57}Co-B_{12}$ and $B_{12}$ analogues. The water was then removed and taken to dryness under vacuum. Each dried fraction was then dissolved in 2.5 ml of water and assayed for $^{57}Co-B_{12}$ and for vitamin $B_{12}$ using a variety of binding proteins. The final recovery of $^{57}Co-B_{12}$ was 64%. The apparent recoveries of vitamin $B_{12}$ were 75% when using human IF in the assay and 66% when using human R in the assay. The results of the assays employing the 38 fractions obtained by paper chromatography are presented in Tables IVA, IVB, and IVC. Similar data concerning paper chromatography of $^{57}Co-B_{12}$ and pure vitamin $B_{12}$, for reference as a control, are presented in Table IVD. The data in these several chromatography tables summarized for convenience in Table IVE reveals that the behavior of $^{57}Co-B_{12}$ that was extracted from human plasma did not change its chromatographic behavior, and thus was not altered during the standard extraction procedure or any of the purification steps. In a similar manner it is postulated that true vitamin $B_{12}$ is not altered in any of the purification or process steps of the assay.

Table IVA

[$^{57}$Co] $B_{12}$ and plasma $B_{12}$ assayed after elution from paper chromatography. All assays were performed at pH 9.0 except where indicated.

| | [$^{57}$Co] $B_{12}$ | | $B_{12}$ assayed with various binders | | | | | | | | |
|---|---|---|---|---|---|---|---|---|---|---|---|
| | | | Human R | | pH 1.8 Human R | | Hog R | | pH 1.8 Hog R | | Hog IFC | |
| Fraction # | (cmp) | (%) | (ng) | (%) | (ng) | (%) | (ng) | (%) | (ng) | (%) | (ng) | (%) |
| 1 | | | 2 | | 1 | | 1 | | 1 | | 1 | |
| 2 | | | | | | | | | | | | |
| 3 | | | | | | | | | | | | |
| 4 | | | 1 | | 1 | | 1 | | 2 | | 1 | |
| 5 | | | 2 | | | | 2 | | 3 | | 2 | |
| 6 | | | 3 | | 3 | | 2 | | 4 | | 2 | |
| 7 | | | 4 | | 4 | | 4 | | 5 | | 3 | |
| 8 | | | 4 | | 3 | | 4 | | 5 | | 3 | |
| 9 | | | 7 | 1 | 6 | | 6 | 1 | 8 | 1 | 5 | 1 |
| 10 | 300 | 1 | 24 | 2 | 29 | 2 | 26 | 2 | 29 | 2 | 16 | 2 |
| 11 | 500 | 2 | 42 | 3 | 54 | 4 | 36 | 3 | 49 | 3 | 26 | 3 |
| 12 | 300 | 1 | 25 | 2 | 34 | 2 | 26 | 2 | 38 | 2 | 19 | 2 |
| 13 | 200 | 1 | 31 | 2 | 44 | 3 | 30 | 3 | 55 | 4 | 22 | 2 |
| 14 | 4600 | 20 | 209 | 16 | 235 | 16 | 176 | 16 | 240 | 16 | 180 | 17 |
| 15 | 14000 | 61 | 562 | 42 | 615 | 43 | 461 | 41 | 576 | 37 | 474 | 46 |
| 16 | 2100 | 9 | 103 | 8 | 122 | 9 | 84 | 7 | 122 | 8 | 91 | 9 |
| 17 | 300 | 1 | 85 | 6 | 118 | 8 | 85 | 8 | 128 | 8 | 53 | 5 |
| 18 | 300 | 1 | 68 | 5 | 68 | 5 | 68 | 6 | 100 | 6 | 45 | 4 |
| 19 | 200 | 1 | 23 | 2 | 17 | 1 | 17 | 2 | 27 | 2 | 15 | 1 |
| 20 | | | 45 | 3 | 39 | 3 | 39 | 3 | 60 | 4 | 24 | 2 |
| 21 | | | 42 | 3 | 25 | 2 | 25 | 2 | 52 | 3 | 21 | 2 |
| 22 | | | 8 | 1 | 5 | | 7 | 1 | 8 | 1 | 5 | 1 |
| 23 | | | 8 | 1 | 4 | | 5 | | 8 | 1 | 4 | |
| 24 | | | 7 | 1 | 4 | | 5 | | 7 | | 3 | |
| 25 | | | 9 | 1 | 1 | | 6 | 1 | 3 | | 4 | |
| 26 | | | 16 | 1 | 1 | | 10 | 1 | 4 | | 5 | 1 |
| 27 | | | 5 | | 1 | | 3 | | 2 | | 2 | |
| 28 | | | 2 | | | | 1 | | 1 | | 1 | |
| 29 | | | 4 | | | | 2 | | 1 | | 2 | |

Table IVA-continued

[57Co] B12 and plasma B12 assayed after elution from paper chromatography.
All assays were performed at pH 9.0 except where indicated.

| | | | | | pH 1.8 | | | pH 1.8 | | |
|---|---|---|---|---|---|---|---|---|---|---|
| | [57Co] B12 | | Human R | | Human R | | Hog R | | Hog R | Hog IFC |
| Fraction # | (cmp) | (%) | (ng) | (%) | (ng) | (%) | (ng) | (%) | (ng) (%) | (ng) (%) |
| 30 | | | 1 | | | | 1 | | | 1 |
| 31 | | | 1 | | | | | | | |
| 32 | | | | | | | | | | |
| 33 | | | | | | | | | | |
| 34 | | | | | | | | | | |
| 35 | | | | | | | | | | |
| 36 | | | | | | | | | | |
| 37 | | | | | | | | | | |
| 38 | | | | | | | | | | |

Table IVB

Assay of [57Co] B12 and plasma B12 after elution from paper chromatography.
All assays were performed at pH 9.0.

| | [57Co] B12 | | Human IF | | Hog IF | | Rabbit IF | |
|---|---|---|---|---|---|---|---|---|
| Fraction # | (cpm) | (%) | (ng) | (%) | (ng) | (%) | (ng) | (%) |
| 1 | | | 1 | | | | 1 | |
| 2 | | | | | | | | |
| 3 | | | | | | | | |
| 4 | | | | | | | | |
| 5 | | | | | 1 | | 1 | |
| 6 | | | | | 1 | | | |
| 7 | | | | | 1 | | 1 | |
| 8 | | | | | 1 | | 1 | |
| 9 | | | 1 | | 1 | | 2 | |
| 10 | 300 | 1 | 4 | 1 | 5 | 1 | 8 | 1 |
| 11 | 500 | 2 | 7 | 1 | 10 | 1 | 16 | 2 |
| 12 | 300 | 1 | 5 | 1 | 7 | 1 | 10 | 1 |
| 13 | 200 | 1 | 14 | 2 | 10 | 1 | 13 | 1 |
| 14 | 4600 | 20 | 169 | 21 | 169 | 22 | 170 | 19 |
| 15 | 1400 | 61 | 488 | 61 | 450 | 57 | 480 | 55 |
| 16 | 2100 | 9 | 73 | 9 | 72 | 9 | 87 | 10 |
| 17 | 300 | 1 | 17 | 2 | 25 | 3 | 42 | 5 |
| 18 | 300 | 1 | 11 | 1 | 15 | 2 | 25 | 3 |
| 19 | 200 | 1 | 3 | | 5 | 1 | 5 | 1 |
| 20 | | | 5 | 1 | 7 | 1 | 8 | 1 |
| 21 | | | 2 | | 4 | 1 | 4 | |
| 22 | | | | | | | | |
| 23 | | | | | | | | |
| 24 | | | | | | | | |
| 25 | | | | | | | | |
| 26 | | | | | | | | |
| 27 | | | | | | | | |
| 28 | | | | | | | | |
| 29 | | | | | | | | |
| 30 | | | | | | | | |
| 31 | | | | | | | | |
| 32 | | | | | | | | |
| 33 | | | | | | | | |
| 34 | | | | | | | | |
| 35 | | | | | | | | |
| 36 | | | | | | | | |
| 37 | | | | | | | | |
| 38 | | | | | | | | |

Table IVC

Assay of [57Co] B12 and plasma B12 after elution from paper chromatography.
All assays were performed at pH 9.0.

| | [57Co] B12 | | Hog IFC | | Hog IFC + Cobinamide | | Hog IFC + CN-Cbl[bde-OH] | | Hog IFC + [3,5,6-Me3BZA] (CN, OH)Cba | | Hog IFC Digested | |
|---|---|---|---|---|---|---|---|---|---|---|---|---|
| Fraction # | (cpm) | (%) | (ng) | (%) | (ng) | (%) | (ng) | (%) | (ng) | (%) | (ng) | (%) |
| 1 | | | 1 | | | | | | | | 1 | |
| 2 | | | | | | | | | | | | |
| 3 | | | | | | | | | | | | |
| 4 | | | 1 | | | | 1 | | 1 | | 1 | |
| 5 | | | 2 | | | | 1 | | 1 | | 1 | |
| 6 | | | 2 | | | | 1 | | 1 | | 1 | |
| 7 | | | 3 | | | | 1 | | 1 | | 2 | |
| 8 | | | 3 | | 1 | | 1 | | 1 | | 2 | |
| 9 | | | 5 | 1 | 1 | | 1 | | 2 | | 3 | |
| 10 | 300 | 1 | 16 | 2 | 4 | | 5 | 1 | 7 | 1 | 9 | 1 |
| 11 | 500 | 2 | 26 | 3 | 10 | 1 | 10 | 1 | 13 | 2 | 15 | 2 |
| 12 | 300 | 1 | 19 | 2 | 8 | 1 | 8 | 1 | 9 | 1 | 11 | 1 |
| 13 | 200 | 1 | 22 | 2 | 9 | 1 | 10 | 1 | 12 | 2 | 14 | 2 |
| 14 | 4600 | 20 | 180 | 17 | 174 | 21 | 170 | 22 | 148 | 20 | 153 | 19 |
| 15 | 14000 | 61 | 474 | 46 | 474 | 58 | 435 | 55 | 396 | 53 | 402 | 50 |
| 16 | 2100 | 9 | 91 | 9 | 83 | 10 | 81 | 10 | 80 | 11 | 84 | 10 |
| 17 | 300 | 1 | 53 | 5 | 25 | 3 | 27 | 3 | 34 | 4 | 36 | 4 |
| 18 | 300 | 1 | 45 | 4 | 16 | 2 | 19 | 2 | 21 | 3 | 27 | 3 |
| 19 | 200 | 1 | 15 | 1 | 4 | | 4 | 1 | 6 | 1 | 9 | 1 |
| 20 | | | 24 | 2 | 7 | 1 | 7 | 1 | 11 | 1 | 13 | 2 |
| 21 | | | 21 | 2 | 3 | | 4 | 1 | 7 | 1 | 9 | 1 |
| 22 | | | 5 | 1 | | | | | 1 | | 2 | |
| 23 | | | 4 | | | | | | 1 | | | |
| 24 | | | 3 | | | | | | | | 1 | |

Table IVC-continued

Assay of [$^{57}$Co] B$_{12}$ and plasma B$_{12}$ after elution from paper chromatograpy.
All assays were performed at pH 9.0.

| | | | | B$_{12}$ assayed with various binders | | | | | |
|---|---|---|---|---|---|---|---|---|---|
| | [$^{57}$Co] B$_{12}$ | Hog IFC | | Hog IFC + Cobinamide | Hog IFC + CN-Cbl[bde-OH] | | Hog IFC + [3,5,6-Me$_3$BZA] (CN, OH)Cba | Hog IFC Digested | |
| Fraction # | (cpm) | (ng) | (%) | (ng) (%) | (ng) | (%) | (ng) (%) | (ng) | (%) |
| 25 | | 4 | | | | | 2 | | |
| 26 | | 5 | 1 | | | | | 2 | |
| 27 | | 2 | | | | | | | |
| 28 | | 1 | | | | | | 1 | |
| 29 | | 2 | | | | | | | |
| 30 | | 1 | | | | | | | |
| 31 | | | | | | | | | |
| 32 | | | | | | | | | |
| 33 | | | | | | | | | |
| 34 | | | | | | | | | |
| 35 | | | | | | | | | |
| 36 | | | | | | | | | |
| 37 | | | | | | | | | |
| 38 | | | | | | | | | |

Table IVD

Assay of [$^{57}$Co] B$_{12}$ and native B$_{12}$ after elution from paper chromatography. All assays were performed at pH 9.0.

| | | | B$_{12}$ assayed with various binders | | | | | |
|---|---|---|---|---|---|---|---|---|
| | [$^{57}$Co] B$_{12}$ | | Human R | | Human IF | | Hog IFC | |
| Fraction # | (cpm) | (%) | (ng) | (%) | (ng) | (%) | (ng) | (%) |
| 1 | | | | | | | | |
| 2 | | | | | | | | |
| 3 | | | | | | | | |
| 4 | | | | | | | | |
| 5 | | | | | | | | |
| 6 | | | | | | | | |
| 7 | | | | | | | | |
| 8 | | | | | | | | |
| 9 | | | | | | | | |
| 10 | 200 | 1 | 1 | | | | 1 | |
| 11 | 600 | 2 | 1 | | 1 | | 2 | 1 |
| 12 | 400 | 1 | 1 | | 1 | | 2 | 1 |
| 13 | 400 | 1 | 4 | 1 | 3 | 1 | 6 | 2 |
| 14 | 6800 | 24 | 86 | 25 | 86 | 26 | 90 | 27 |
| 15 | 15800 | 56 | 210 | 60 | 198 | 60 | 189 | 56 |
| 16 | 3100 | 11 | 40 | 12 | 38 | 12 | 40 | 12 |
| 17 | 200 | 1 | 2 | 1 | 1 | | 3 | 1 |
| 18 | 200 | 1 | 2 | 1 | 1 | | 2 | 1 |
| 19 | 100 | | 1 | | | | 2 | 1 |
| 20 | | | | | | | | |
| 21 | | | | | | | | |
| 22 | | | | | | | | |
| 23 | | | | | | | | |
| 24 | | | | | | | | |
| 25 | | | | | | | | |
| 26 | | | | | | | | |
| 27 | | | | | | | | |
| 28 | | | | | | | | |
| 29 | | | | | | | | |
| 30 | | | | | | | | |
| 31 | | | | | | | | |
| 32 | | | | | | | | |
| 33 | | | | | | | | |
| 34 | | | | | | | | |
| 35 | | | | | | | | |
| 36 | | | | | | | | |
| 37 | | | | | | | | |
| 38 | | | | | | | | |

Table IV E

Summary of the data in Tables IVA - IVD involving assays of [$^{57}$Co] B$_{12}$ and B$_{12}$ after elution from paper chromatography. Assays for B$_{12}$ were performed at pH 9.0 except where indicated

| | | | Chromatogram Fractions | | | | | | | |
|---|---|---|---|---|---|---|---|---|---|---|
| | | | 1–13 | | 14–16 | | 17–38 | | 1–38 | |
| Sample Chromatographed | Item Assayed | Assay Binder | (ng) | (%) | (ng) | (%) | (ng) | (%) | (ng) | (%) |
| [$^{57}$Co] B$_{12}$ + B$_{12}$ | [$^{57}$Co] B$_{12}$ | — | — | 5 | — | 92 | — | 2 | — | 100 |
| " | B$_{12}$ | Human R | 7 | 2 | 336 | 97 | 5 | 1 | 348 | 100 |
| " | B$_{12}$ | Human IF | 5 | 1 | 322 | 98 | 2 | 1 | 329 | 100 |
| " | B$_{12}$ | Hog IFC | 11 | 3 | 319 | 95 | 7 | 2 | 337 | 100 |
| [$^{57}$Co] B$_{12}$ + plasma B$_{12}$ | [$^{57}$Co] B$_{12}$ | | — | 6 | — | 91 | — | 3 | — | 100 |
| " | B$_{12}$ | Human R | 145 | 11 | 874 | 65 | 324 | 24 | 1343 | 100 |
| " | B$_{12}$ | Human R (pH 1.8) | 179 | 12 | 972 | 68 | 283 | 20 | 1434 | 100 |
| " | B$_{12}$ | Hog R | 138 | 12 | 721 | 64 | 274 | 24 | 1133 | 100 |
| " | B$_{12}$ | Hog R (pH 1.8) | 199 | 13 | 938 | 61 | 402 | 26 | 1539 | 100 |
| " | B$_{12}$ | Hog IFC | 100 | 10 | 745 | 72 | 185 | 18 | 1030 | 100 |
| " | B$_{12}$ | Human IF | 31 | 4 | 730 | 91 | 38 | 5 | 799 | 100 |
| " | B$_{12}$ | Hog IF | 37 | 5 | 691 | 88 | 56 | 7 | 784 | 100 |
| " | B$_{12}$ | Rabbit IF | 53 | 6 | 737 | 84 | 84 | 10 | 874 | 100 |
| " | B$_{12}$ | Hog IFC + Cobinamide | 32 | 4 | 731 | 89 | 54 | 7 | 818 | 100 |
| " | B$_{12}$ | Hog IFC + CN-Cbl[bde-OH] | 47 | 6 | 624 | 83 | 81 | 11 | 752 | 100 |
| " | B$_{12}$ | Hog IFC + | 38 | 5 | 686 | 87 | 61 | 8 | 785 | 100 |

Table IV E-continued

Summary of the data in Tables IVA - IVD involving assays of [$^{57}$Co] $B_{12}$ and $B_{12}$ after elution from paper chromatography. Assays for $B_{12}$ were performed at pH 9.0 except where indicated

| Sample Chromatographed | Item Assayed | Assay Binder | Chromatogram Fractions | | | | | | | |
|---|---|---|---|---|---|---|---|---|---|---|
| | | | 1-13 | | 14-16 | | 17-38 | | 1-38 | |
| | | | (ng) | (%) | (ng) | (%) | (ng) | (%) | (ng) | (%) |
| " | $B_{12}$ | [3,5,6-Me$_3$BZA] (CN, OH)Cba Hog IFC — Digested | 60 | 7 | 639 | 80 | 102 | 13 | 801 | 100 |

Referring to the control chromatogram of Table IVD, it is seen that the several RID assays of pure vitamin $B_{12}$ performed variously with human R protein, human IF protein and hog IFC gave substantially a single symmetrical peak of activity. In each instance greater than 95% of the vitamin $B_{12}$ was found to be present in fraction 14 through 16. Similar results, as shown in Table IVB, were obtained from the paper chromatogram of the plasma extract when the binding protein was human IF, hog IF and rabbit IF. These data are an indication that these three IF binding proteins are substantially specific in their binding ability to vitamin $B_{12}$, and substantially non-reactive with vitamin $B_{12}$ analogues present in plasma.

Efforts were made to modify hog IFC, which is a commonly used binder in RID assays and which has been found to contain as much as 90% hog R protein and as little as 10% hog IF, by removing or inactivating the hog R. In several instances the hog IFC was incubated with an excess amount of three chemically synthesized vitamin $B_{12}$ analogues before it was utilized in the RID assay. Referring to Table IVC, it is seen that after this modification the chromatogram results obtained utilizing the modified hog IFC closely resemble the results obtained with substantially pure hog IF. It is therefore seen, that in the practice of the present invention, mixtures of protein including both vitamin $B_{12}$ specific binding protein and binding protein which is not specific to vitamin $B_{12}$ can be modified by the addition of an excess amount of vitamin $B_{12}$ analogue, by which process the analogue binds with the non-specific protein to render it substantially bound or inactive so that it is not available to react with vitamin $B_{12}$ or ($^{57}$Co) $B_{12}$ present in samples undergoing RID tests. The amount of vitamin $B_{12}$ analogue to be added to a mixture of specific and non-specific proteins in order to bind or inactivate the non-specific proteins may vary over a wide range, depending on both the proteins which are present and the vitamin $B_{12}$ analogues which are utilized as the binding or inactivating material. Generally speaking, for the examples shown in Table IVC, cobinamide may be added in an amount equal to that required for complete binding of the non-specific protein, up to amount as much as ten million times greater than the amount needed to bind the protein, with the preferred range being about ten to about ten thousand times in excess of that required for complete binding. CN-Cbl (bde-OH), known as CoB-cyano-cobamic a,c,g-triamide may be utilized in an amount at least about ten times to about ten million times in excess of the amount required to bind with the non-specific protein, with an amount of about one hundred to about one hundred thousand times excess being preferred. The (3,5,6-Me$_3$BZA) (CN,OH)-cba, known as Co$\alpha$(3,5,6-trimethylbenzimidazole) cobamide should also be utilized in amounts from about one to ten million times in excess of the amount of non-specific protein, with an amount in the range of about ten to about ten thousand times excess being preferred. Suitable amounts of other vitamin $B_{12}$ analogues may be utilized in a similar manner to bind or inactivate non-specific proteins present in mixtures with specific proteins in order to obtain a preparation of binding protein which will substantially bind only $^{57}$Co-$B_{12}$, or the vitamin $B_{12}$ naturally present in the samples being tested, and thus give a more accurate quantitative RID assay of vitamin $B_{12}$ in samples undergoing tests.

Again, referring to Table IVC, data on samples of hog IFC digested with trypsin and chymotrypsin are shown. These and other proteolytic enzymes are specific in their ability to substantially digest R proteins while leaving intrinsic factor proteins unaffected and available as substantially the only protein for binding $^{57}$Co-$B_{12}$ and vitamin $B_{12}$ in RID assays. Other enzymes, including, for example, elastase may be utilized for the same purpose. The amount of the enzymes utilized is in the range of about 0.01 to about 100 milligrams per mililiter of protein treated, with a preferred amount being about 0.05 to about 40 milligrams per mililiter of protein. Utilizing this proteolytic enzyme digestion process a protein binder is provided which substantially binds only $^{57}$Co-$B_{12}$ and vitamin $B_{12}$ and is not affected by vitamin $B_{12}$ analogues in the samples being tested and which therefore gives a more accurate RID assay than is obtained when utilizing the original mixture of hog IFC proteins which included non-specific proteins which would have been capable of reacting with the newly discovered vitamin $B_{12}$ analogues in samples to give inaccurate assays as to the amount of vitamin $B_{12}$ in test samples.

Now, referring to Table IVA, when samples from the plasma extract chromatogram were assayed for vitamin $B_{12}$ with human R, hog R and hog IFC, different results were obtained than when those samples were assayed with human IF, hog IF, rabbit IF or hog IFC treated with vitamin $B_{12}$ analogues or hog IFC digested with proteolytic enzymes. In each case where human R, hog R or untreated hog IFC were utilized as the binding protein the tests gave the appearance that more vitamin $B_{12}$ was present in the chromatogram samples, especially in fractions 1 through 13 and 17 through 38. This observation, when taken with the above data, provides strong evidence that normal human plasma contains a number of vitamin $B_{12}$ analogues that compete with $^{57}$Co-$B_{12}$, in significant amounts, for binding to R protein. It also indicates that such activity on the part of the $B_{12}$ analogues is substantially absent when the binding protein utilized in the RID assay is substantially specific to vitamin $B_{12}$.

It should also be noted, see Table IVA, that the chromatogram data suggests that the lack of specificity of human R and hog R is unchanged when RID assays are performed at acid pH. This indicates that erroneous results will be obtained for the true vitamin $B_{12}$ content of samples which contain vitamin $B_{12}$ analogues when RID assays are performed at acid pH.

Using the same techniques and criteria described above it has been discovered that vitamin $B_{12}$ analogues are not only present in serum obtained from human blood, but are also present in mammalian tissues in even higher concentrations than they are in blood. Vitamin $B_{12}$ analogues extracted from mammalian tissues have been purified using the same schemes as described above. When analyzed utilizing paper chromatography, they exhibited similar mobilities to those of the vitamin $B_{12}$ analogues observed in the samples extracted from blood serum. Since larger amounts of the vitamin $B_{12}$ analogues are present in tissue, they can be observed visually as red or orange spots during paper chromatography. The absorption spectra of vitamin $B_{12}$ analogues purified from tissue extracts have been determined and demonstrate that they are similar to, but distinct from, the absorption spectrum of true vitamin $B_{12}$. These observations provide additional evidence that the materials in blood serum which preferentially react with R proteins and not intrinsic factor proteins are in fact varieties of vitamin $B_{12}$ analogues.

The newly discovered vitamin $B_{12}$ analogues also differ from vitamin $B_{12}$ in terms of their biological activity. Thus, as shown in Table V, the serum vitamin $B_{12}$ values obtained with *Euglena gracilis* for eleven patients diagnosed to have vitamin $B_{12}$ deficiency were substantially similar to the results obtained by RID assay using human IF or hog IF as the binding protein.

vitamin $B_{12}$ activity of the type which is required to promote the growth of *Euglena gracilis*.

Data was obtained on ten additional patients diagnosed to be vitamin $B_{12}$ deficient and the total of 21 patients with vitamin $B_{12}$ deficiency are shown in Table V. In each of the 21 patients the vitamin $B_{12}$ values found when the RID assay was carried out utilizing human IF or hog IF were below the range of vitamin $B_{12}$ values found in a control group of 74 normal subjects. However, when the RID assay was carried out utilizing human R or hog R only about half of the 21 vitamin $B_{12}$ deficient patients were found to assay below the range of normal subjects for vitamin $B_{12}$. This indicates that where the newly found vitamin $B_{12}$ analogues are present in the samples being tested, and the binding protein is not specific to vitamin $B_{12}$, the resulting assays may suggest that a truly vitamin $B_{12}$ deficient patient is not within the deficient range. This may lead to delay of treatment of that patient for vitamin $B_{12}$ deficiency. It also indicates that the vitamin $B_{12}$ analogues that have now been discovered lack the therapeutic or beneficial activity of vitamin $B_{12}$ in the sense of being unable to prevent the hematologic and/or neurologic abnormalities associated with vitamin $B_{12}$ deficiency.

There are many commercial RID assay type kits available for the assay of vitamin $B_{12}$ in clinical laboratories. Table VI sets forth an analysis of several such kits, and a comparison of the types of protein found in those kits with hog IF, hog R and hog IFC. By reference to Table VI, it is seen that the commercial kits appear to have only about 13% to about 35% intrinsic Table V

| | Vitamin $B_{12}$ levels in 21 patients with clinical evidence of vitamin $B_{12}$ deficiency | | | | |
|---|---|---|---|---|---|
| | Vitamin $B_{12}$ assayed with various binders | | | | Vitamin $B_{12}$ assayed |
| Patient | Human R (pg/ml) | Hog R (pg/ml) | Human IF (pg/ml) | Hog IF (pg/ml) | with Euglena Gracilis (pg/ml) |
| 1 | 155 | 138 | 16 | 0 | 43 |
| 2 | 310 | 295 | 51 | 86 | 52 |
| 3 | 310 | 255 | 24 | 35 | 46 |
| 4 | 135 | 132 | 0 | 22 | 40 |
| 5 | 215 | 250 | 52 | 60 | 25 |
| 6 | 347 | 342 | 0 | 0 | 56 |
| 7 | 102 | 120 | 0 | 0 | 35 |
| 8 | 240 | 242 | 58 | 65 | 79 |
| 9 | 160 | 125 | 38 | 23 | 0 |
| 10 | 85 | 84 | 0 | 12 | 23 |
| 11 | 235 | 255 | 5 | 11 | 0 |
| 12 | 188 | 190 | 41 | 38 | |
| 13 | 178 | 192 | 48 | 38 | |
| 14 | 298 | 305 | 53 | 57 | |
| 15 | 355 | 310 | 78 | 82 | |
| 16 | 178 | 210 | 48 | 22 | |
| 17 | 128 | 140 | 31 | 8 | |
| 18 | 106 | 190 | 50 | 40 | |
| 19 | 163 | 155 | 0 | 0 | |
| 20 | 178 | 132 | 25 | 0 | |
| 21 | 230 | 215 | 75 | 41 | |
| Mean (1–11) | 209 | 203 | 22 | 29 | 36 |
| Mean (1–21) | 205 | 204 | 33 | 30 | |
| Normal Range (mean ± 2 std. dev.) | 220–1230 | 245–1230 | 136–656 | 157–717 | (>130) |
| Number within normal range | 9 (43%) | 10 (48%) | 0 | 0 | 0 |

It is to be further noted, that all of the values obtained by either microbiologic assay or by assay using human IF or hog IF were substantially lower than the values obtained when the RID assay was carried out utilizing human R or hog R as the binding protein. This indicates that the vitamin $B_{12}$ analogues which have now been identified in mammalian blood and tissue do not possess factor and from about 60% to about 85% R protein. It is therefore suspected, that the use of these kits will give substantially erroneous assays of the amount of vitamin $B_{12}$ present in a sample when the sample also includes vitamin $B_{12}$ analogues, such as those newly discovered to exist in mammalian blood and tissues. It has also been determined that the effectiveness of intrinsic factor to bind vitamin $B_{12}$ is somewhat pH dependent, with intrinsic factor losing about 10% of its binding ability at a pH of about 4.1 and losing about 99% of its binding ability at a pH of about 1.9. Thus, to the extent that the commercial kits use a pH of about 4.1 during binding they would have about 10%l less intrinsic factor than shown in Table VI. Those kits having a pH during-binding of about 1.7 to about 1.9 would obtain substantially no binding from intrinsic factor.

Table VI

Analysis of vitamin $B_{12}$ binders and assay pH used in commercial kits sold for the assay of vitamin $B_{12}$ in clinical laboratories

| Source of Binder | Vitamin $B_{12}$ Binding Protein | | Assay pH of kit[d] |
|---|---|---|---|
| | intrinsic factor[a] (%) | R protein[b] (%) | |
| Hog IF | 97 | 0 | — |
| Hog R | 0 | 98 | — |
| Hog IFC | 25 | 75 | — |
| Diagnostic Products Corp. Kit | 35 | 60 | 1.7 |
| New England Nuclear Kit | 20 | 82 | 4.1 |
| Bio-Rad Laboratories Kit | 30 | 71 | 1.9 |
| Medvak Diagnostic Products Kit | 13 | 85 | 1.8 |
| Schwarz/Mann Kit | 34 | 67 | 9.1 |
| Pharmacia Diagnostics Kit | 1 (33)[c] | 67 | 4.1 |

[a] Inhibition of [$^{57}$Co] $B_{12}$ binding observed with anti-IF antibodies at pH 7.5.
[b] Inhibition of [$^{57}$Co] $B_{12}$ binding observed with a 100 fold molar excess of cobinamide at pH 7.5.
[c] In this kit the binder is covalently attached to an insoluble matrix and because of steric factors it may not be accessible to anti-intrinsic factor antibodies. Thus the value for % intrinsic factor may be as high as 33%.
[d] Refers to the pH measured after the addition of all of the components of each individual kit. R protein retains its full $B_{12}$ binding ability over the range of pH 1.7-9.1 but intrinsic factor loses 10% and 99% of its $B_{12}$ binding ability % intrinsic factor than is indicated in the table while those that use pH 1.7-1.9 are employing essentially no intrinsic factor.

While the invention has been particularly shown and described with reference to preferred embodiments thereof, it will be understood by those skilled in the art that the foregoing and other modifications or changes in form and details may be made therein without departing from the spirit and scope of the invention.

What is claimed is:

1. A radioisotope dilution assay for measuring the vitamin $B_{12}$ level in a sample comprising:
   contacting said sample with a known amount of a radioisotope of vitamin $B_{12}$ and a composition containing a binding protein substantially specific to vitamin $B_{12}$, said composition being substantially free of substances which bind vitamin $B_{12}$ analogues.

2. The method of claim 1 wherein the source of vitamin $B_{12}$ is selected from the group consisting of mammalian tissue and mammalian blood.

3. The method of claim 1 wherein the source of vitamin $B_{12}$ is human blood.

4. The method of claim 1 wherein the binding protein is intrinsic factor.

5. The method of claim 4 wherein the binding protein consists essentially of protein selected from the group consisting of human IF, hog IF and rabbit IF.

6. The method of measuring vitamin $B_{12}$ analogues present in a sample which also includes vitamin $B_{12}$, including the steps of:
   assaying a portion of the sample with a binder which is a binder for both vitamin $B_{12}$ and vitamin $B_{12}$ analogues;
   assaying a portion of the sample with a binder which is substantially specific to vitamin $B_{12}$ and substantially free of substances which bind vitamin $B_{12}$ analogues; and
   then determining the difference between the two assays as being substantially indicative of the amount of vitamin $B_{12}$ analogue in the sample.

* * * * *